(12) United States Patent
Karpishin et al.

(10) Patent No.: US 6,391,648 B1
(45) Date of Patent: May 21, 2002

(54) PHOTOLUMINESCENT METAL-(BIS) LIGAND COMPLEXES HAVING DIFFERENT LIGANDS

(75) Inventors: Timothy B. Karpishin; Mark T. Miller, both of San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/510,887

(22) Filed: Feb. 23, 2000

Related U.S. Application Data

(60) Provisional application No. 60/121,535, filed on Feb. 25, 1999.

(51) Int. Cl.[7] .................................................. G01N 21/76
(52) U.S. Cl. ...................................................... 436/172
(58) Field of Search .......................... 422/82.07, 82.05; 436/518, 73, 172

(56) References Cited

U.S. PATENT DOCUMENTS

| | | | | |
|---|---|---|---|---|
| 5,393,903 A | * | 2/1995 | Gratzel et al. | 556/137 |
| 5,814,575 A | * | 9/1998 | Reagan et al. | 502/117 |
| 6,060,614 A | * | 5/2000 | Orvig et al. | 556/13 |
| 6,212,093 B1 | * | 4/2001 | Lindsey | 365/151 |

OTHER PUBLICATIONS

Eggleston et al., "Steric Effects in the Ground and Excited States of Cu(NN)$_2^+$ Systems," *Inorg. Chem.*, 36:172–176, 1997.

Stokes et al., "An optical oxygen sensor and reaction essel for high–pressure applications," *Limnol. Oceanogr.*, 44(1):189–195, 1999.

* cited by examiner

*Primary Examiner*—Jill Warden
*Assistant Examiner*—Samuel P Siefke
(74) *Attorney, Agent, or Firm*—Brown, Martin, Haller & McClain

(57) ABSTRACT

Photoluminescent complexes of copper, silver, zinc, lithium or similar metals are described, being (bis)ligand, with two different ligands. A variety of ligands may be used, the larger ligand being of a size or shape such that a pair of such ligand are prevented by steric properties from forming a (bis)ligand complex with the metal. Preferred substituents may be alkyl, aryl or alkaryl hydrocarbons, or halogen, chalcogen, nitrogen or phosphorus moieties, or included heteroatoms. Formation of the (bis)ligand complex is accomplished by maintaining the molar ratios of reactants at that which is equivalent to the (bis)ligand complex composition. The complexes are useful as optical sensors for $O_2$, $NH_3$ and $NO_x$, in dye sensitization for photovoltaic devices/solar cells, in producing visible $TiO_2$ photosensitization and in $H_2$ production from the photochemically splitting water. These heteroleptic complexes exhibit photoluminescence equal to or better than ruthenium homoleptic complexes.

7 Claims, 3 Drawing Sheets

PHOTOLUMINESCENT METAL-(BIS) LIGAND COMPLEXES HAVING DIFFERENT LIGANDS

CROSS-REFERENCE TO RELATED APPLICATION

This invention claims the priority of Provisional Patent Application Ser. No. 60/121,535, filed on Feb. 25, 1999, entitled "Highly Emissive Photoluminescent Copper Complex."

BACKGROUND OF THE INVENTION

1. Field of the Invention

The invention herein relates to photoluminescent metal-ligand complexes. More particularly it relates to novel complexes having extended luminescent lifetime and that are useful as optical oxygen sensors.

2. Description of the Prior Art

Photoluminescent molecules that are based on transition metals have been studied extensively for a number of years. The chemistry and photophysics of these molecules have been thoroughly investigated because of the varying potential applications for the photoluminescent transition-metal complexes. The most widely studied photoluminescent complex has been the tris(2,2'-bipyridyl) complex of ruthenium (II), written as $[Ru(bpy)_3]^{2+}$. The primary properties of $[Ru(bpy)_3]^{2+}$ that are important for most applications are a long excited-state lifetime, strong absorption in the visible region, and a high quantum yield of luminescence.

Although many applications of $[Ru(bpy)_3]^{2+}$ have been investigated, the high cost and low availability of ruthenium are a substantial impediment to large-scale applications of the molecule. Research to find cheaper alternatives to $[Ru(bpy)_3]^{2+}$, such as complexes based on copper, have been investigated, but none have been identified which have the long excited state lifetimes and high quantum yields of luminescence that are observed for the ruthenium-based complexes.

SUMMARY OF THE INVENTION

We have now invented a new class of metal-(bis)ligand complexes which have quantum yields of luminescence that are comparable to that of $[Ru(bpy)_3]^{2+}$. In the solid state, our complexes display excited-state lifetimes that are longer than that observed for $[Ru(bpy)_3]^{2+}$. Because of the cost differential between copper and ruthenium, our complexes cost substantially less than $[Ru(bpy)_3]^{2+}$. These new complexes are anticipated to generate significant large-scale applications which have heretofore not resulted from the $[Ru(bpy)_3]^{2+}$ complexes.

Specifically, the complexes of this invention are based on copper, silver, zinc and lithium, and those other metals, particularly transition metals, which may be found to exhibit complexing properties equivalent to the named metals. (We recognize that lithium as a Group 1 element is commonly classified as an "alkali metal" rather than as a conventional metal of the Groups 3–12. In the present invention, however, lithium exhibits the same complexing properties as copper, zinc and silver, and will therefore be considered to be within the definition of "metal" for the purposes of this invention.)

The complexes of the present invention are (bis)ligand, with the two ligands being different from each other. Preferably the ligands are each a substituted phenanthroline. A wide variety of substituents are possible, subject to the limitation that no significant adverse reactions competitive to the desired complexing reaction are promoted by a particular substituent. Substituents may be alkyl, aryl or alkaryl hydrocarbons, and the hydrocarbons may also be substituted with halogen, chalcogen, nitrogen or phosphorus moieties, or contain heteroatoms. The specific substituents which will work will depend on the steric properties of the pair of substituents being considered. We have found the necessary steric considerations are that one of the substituents must be of a size and shape that prevent a pair of that substituted ligand from complexing with the metal atom (M).

The method of formation of such complexes is also an aspect of the present invention.

Further description and representative examples will be presented below.

DETAILED DESCRIPTION AND PREFERRED EMBODIMENTS

Figure 1:
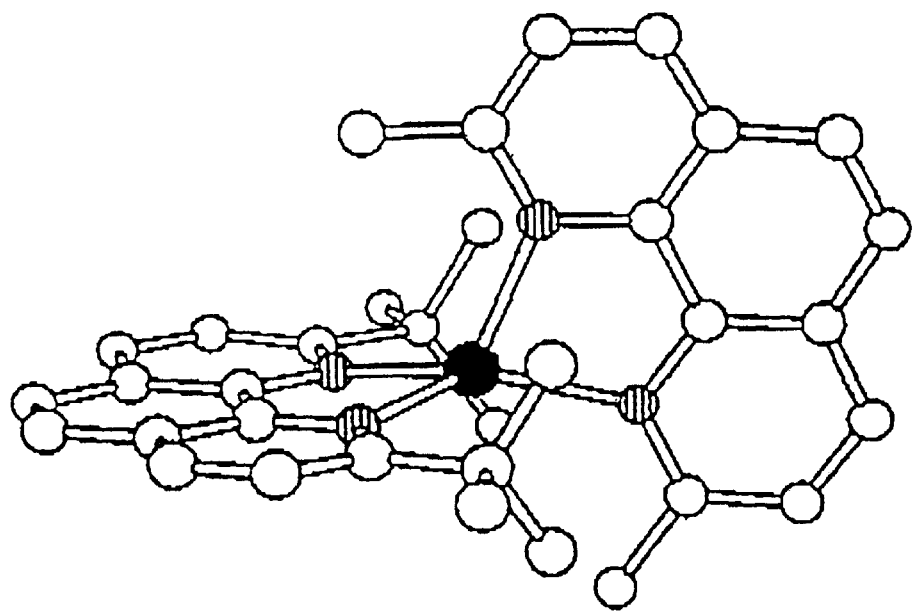
FIG. 1 is an illustration of a ball-and-stick model of a $[Cu(dbp)(dmp)]^+$ complex of the present invention, with the hydrogen atoms omitted for clarity. The atomic representations are: Cu=●, C=○ and N=◐.

The invention will be best understood by consideration of prior art and present complex forming reactions and their products, using copper complexes as examples. The prior art has used single ligands, to avoid forming a mixture of metal-ligand products, which cannot usually be separated into the individual complexes. Further, even for those mixtures for which separation has been accomplished (albeit with substantial difficulty), the separated (bis)ligand complex has been found to degenerate to a mixture of complexes. The prior art can therefore be illustrated as:

  (1)

such as

  (2)

such as $Ru^{++}+3L \rightarrow RuL_3^{++}$, in which M represents a metal and L represents a ligand. The homoleptic reactions with ruthenium have produced successful, but very expensive, photoluminescent complexes, as noted above. Copper homoleptic complexes have also been investigated, but since they have been inferior to the ruthenium homoleptic complexes they have not been pursued.

The prior art, however, has been unable to effectively produce (bis)ligand complexes, because of the formation of inseparable mixtures of complexes according to the following reaction:

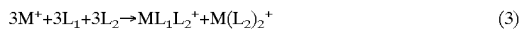

where $L_1$ and $L_2$ represent different ligands.

We have discovered that under carefully defined reaction conditions, with ligands having specific steric relationships to each other and the metal atom, and with specific metals, the chemistry of Reaction (3) can be altered such that high yields of the heteroleptic complex ($ML_1L_2^+$) can be obtain to the virtual exclusion of both of the homoleptic complexes. Thus through this invention one can obtain (bis)ligand complexes which equal or surpass the homoleptic ruthenium complexes which have heretofore been the best available, and can obtain those heteroleptic complexes without need for difficult, and usually unproductive, chemical separation processes.

In the present invention $L_1$ and $L_2$ are different ligands, and in preferred embodiments each is a substituted phenanthroline. A wide variety of substituents are possible, subject to the limitation that no significant adverse reactions competitive to the desired complexing reaction are promoted by a particular substituent. Substituents may be alkyl, aryl or alkaryl hydrocarbons, and the hydrocarbons may also be substituted with halogen, chalcogen, nitrogen or phosphorus moieties, or contain heteroatoms. The specific substituents which will work will depend on the steric properties of the pair of substituents being considered. We have found the necessary steric considerations are that one of the substituents must be of a size and shape that prevent a pair of that substituted ligand from complexing with the metal atom (M). As examples, n-pentyl and t-butyl are sufficiently large and adequately shaped to prevent formation of a di-n-pentyl phenanthroline or di-t-butyl phenanthroline complex, since the steric properties of the two ligands are such that both cannot be simultaneously in complexing proximity with the metal atom to form the required M—N bonds. Conversely, n-butyl is a small enough substituent that a di-n-butyl phenanthroline complex can be formed, and neo-pentyl phenanthroline may form (bis)ligand complexes with some metals but not others; see Eggleston et al., *Inorg. Chem.*, 36:172–176 (1997). Determination of the steric properties of specific ligands of interest for the purpose of this invention will be readily accomplished by those skilled in the art. It is preferred that the two substituents on a given ligand will be identical, so that a ligand described as "methyl-substituted" will be understood to be a dimethyl structure.

(The ligands are often referred to or described as compounds herein for convenience. It will of course be understood that they do not exist as separate compounds once incorporated into the subject complexes.)

Therefore, since one of the substituents in the present complexes cannot sterically form a (bis)ligand complex, the chemistry of Reaction (3) is revised to the following reaction:

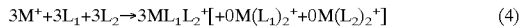

where $L_1$ represents the smaller ligand and $L_2$ represents the larger ligand. The formation of $M(L_1)_2^+$ is not observed, through sterically possible, since the following equilibrium situation will exist:

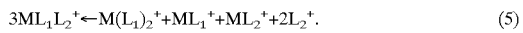

The equilibrium lies far to the left since the formation constants for $M(L)_2^+$ complexes far exceed the formation constants for $M(L)^+$ complexes. Thus, the exclusive formation of the heteroleptic ligand complex is observed. This is accomplished by maintaining equal concentrations of each of the reactants $M^+$, $L_1$ and $L_2$ in the reaction solution.

Figure 4:
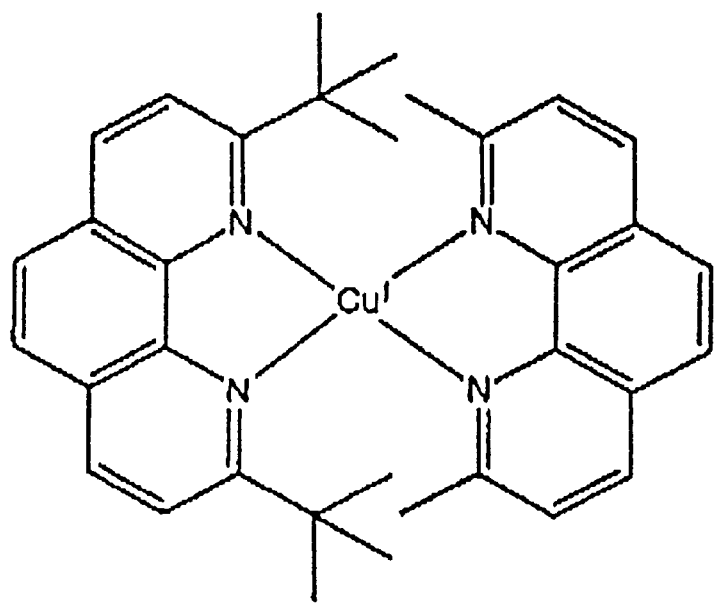
FIG. 4 is a 2-dimensional representation of the complex of FIG. 1, without consideration of the steric aspects of the complex.

It will be seen from FIG. 4 that the preferred ligands of interest in this invention are those which have substituents at the 2- and 9-positions of the phenanthroline. It is possible that other substituents may be present in addition to the 2- and 9-substituents without affecting the formation or function of the complexes, but such will have to be determined on an individual basis.

The metals to be complexed with the described ligands may be copper, silver, zinc and lithium. It is also anticipated that other metals, especially transition metals, may be useful in this invention, if they have the reaction characteristics of the named metals.

There are numerous useful applications for the (bis)ligand complexes of the present invention. These include, but are not restricted to, use as optical oxygen sensors, in dye sensitization for photovoltaic devices/solar cells and in hydrogen production from the photochemical splitting of water. The first use is at present the most direct application of the copper-based complexes, since we have found that the luminescence of the complex exemplified below is very sensitive to oxygen. There have been a large number of studies described in the literature regarding various aspects of optical detection of oxygen. Therefore, while it is possible to make numerous (bis)ligand complexes according to this invention, the preferred complexes will be those which exhibit photoluminescence, since that utility is presently well-established while the applications of other utilities are less studied.

Figure 5:
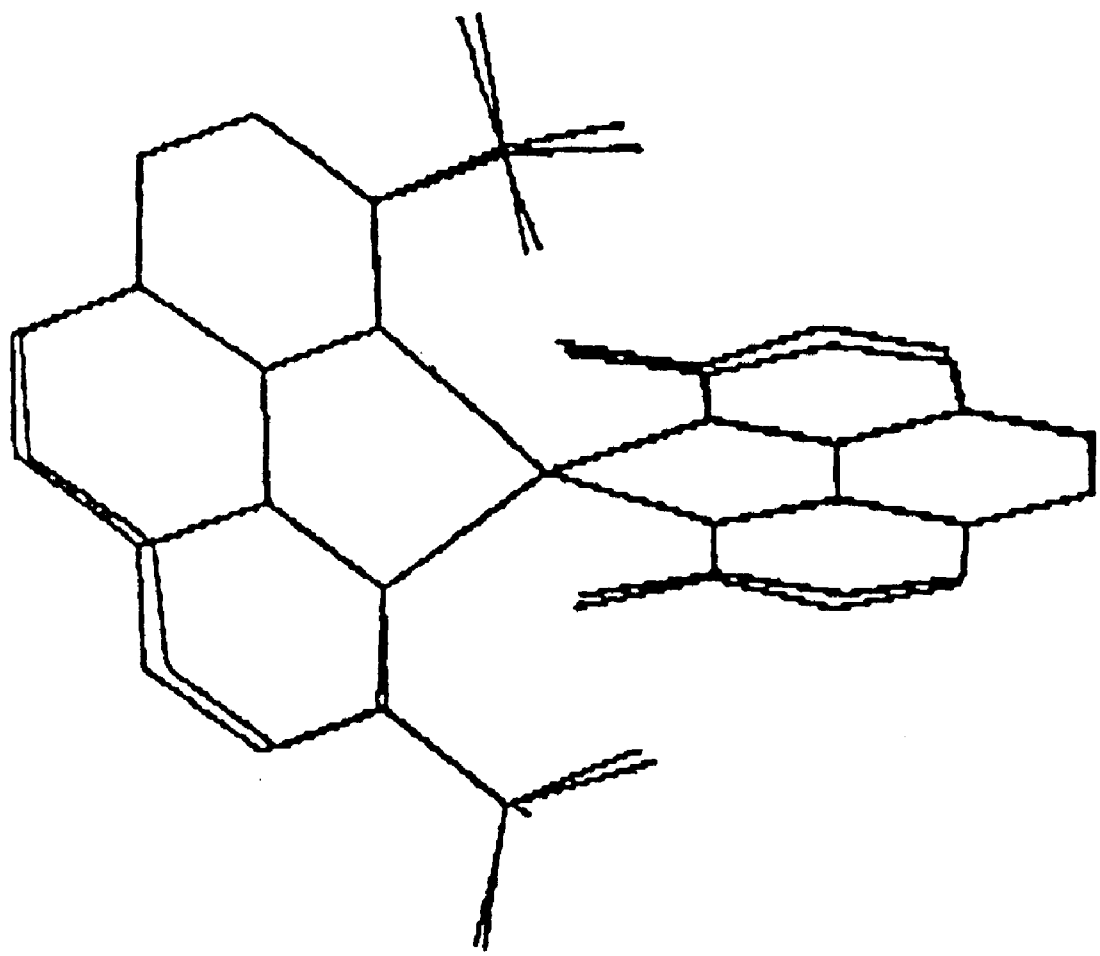
FIG. 5 is a perspective line-illustration of the complex of FIG. 1, for comparison with FIG. 4, but showing the steric considerations typical of the present complexes. In this Figure the (dbp)-substituted ligand is aligned vertically on the left and the (dmp)-substituted ligand is aligned horizontally on the right, with the Cu atom at the "X" at the center.

The invention may be exemplified by description of the preparation and analysis of a copper complex of 2,9-di-t-butyl-1,10-phenanthroline ("dbp") and 2,9-dimethyl-1,10-phenanthroline ("dmp"; also known as neocuproine). The complex [Cu(dbp)(dmp)](PF$_6$) is prepared by first stirring one equivalent of dbp with one equivalent of [Cu(CH$_3$CN)$_4$](PF$_6$) in CH$_2$Cl$_2$ under N$_2$; the compound [Cu(CH$_3$CN)$_4$](PF$_6$) is described in Kubas, *Inorg. Synth.*, 19:90 (1979). The bulky t-butyl groups in dbp prevent formation of [Cu(dbp)$_2$]$^+$. One equivalent of dmp is then added and the solution immediately turns from yellow to deep orange. Recrystallization (MeOH) is sufficient for purification from a small amount of the side-product [Cu(dmp)$_2$](PF$_6$), and yields the air-stable, orange [Cu(dbp)(dmp)](PF$_6$). Analysis of the crystal structure of the complex demonstrates the heteroleptic coordination about the copper ion (see FIGS. 1, 4 and 5). The complex crystallizes in space group P2$_1$, with a=15.489(7)Å, b=11.983(7)Å, c=18.102(13) Å, β=91.23(5)°, V=3359(4)Å$^3$ and Z=4. The coordination geometry is distorted from a D$_{2d}$ pseudo-tetrahedral geometry that might be expected for a d$^{10}$ ion. The geometry is best described as trigonal pyramidal with molecular C$_s$ symmetry, in which the dmp ligand is canted from D$_{2d}$ symmetry along one of the mirror planes. Several structures of the complex cation [Cu(dmp)$_2$]$^+$ have been shown to adopt geometries distorted from D$_{2d}$ symmetry. In most cases, the largest distortion is a flattening of the phenanthroline ligands with respect to each other, usually attributed to crystalpacking forces; see Goodwin et al., *Inorg. Chem.*, 25:2033–2036 (1986) and Dobson et al., *Aust J. Chem.*, 37:649–659 (1984). In the [Cu(dbp)(dmp)](PF$_6$) structure, however, the t-butyl groups of the dbp ligand prevent the flattening distortion and result in a nearly orthogonal orientation of the two phenanthroline planes. In addition, in the complex's structure, there are two independent molecules of [Cu(dbp)(dmp)]$^+$ in the asymmetric unit, with a dihedral angle between the phenanthroline ligands of 90.1° and 90.2° for each of the independent molecules in the asymmetric unit. Each of the complex cations adopts identical trigonal pyramidal geometries (mns error–0.022 Å for the CuN$_4$ cores). Short intermolecular phenanthroline-phenanthroline distances (<3.6 Å) are evident in the unit cell, but it is not known whether packing forces stabilize the observed trigonal pyramidal geometry.

Figure 2:
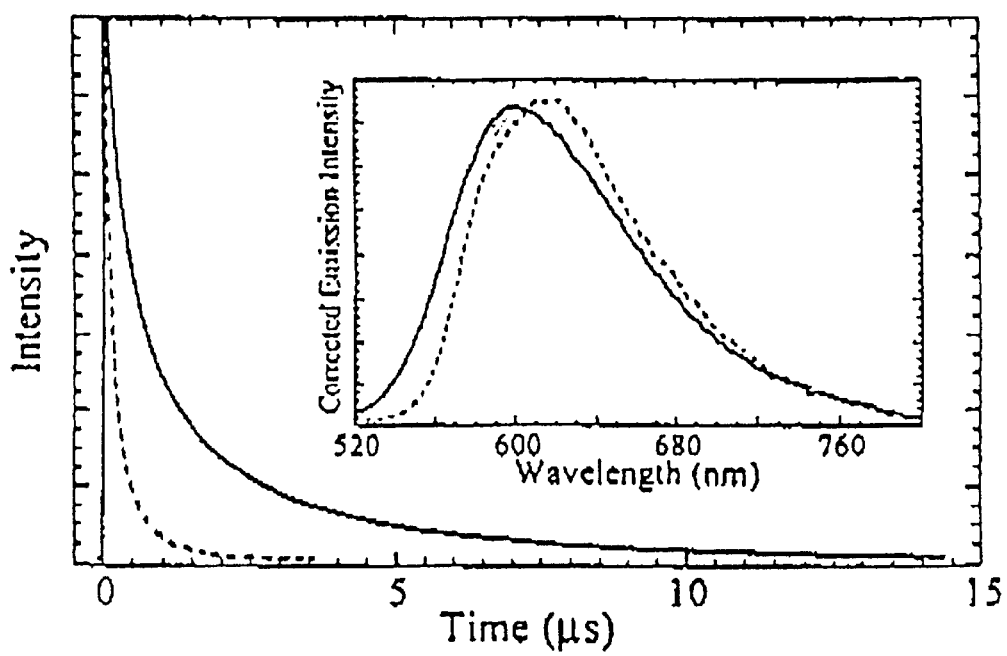
FIG. 2 is a graph comparing time-resolved photoluminescent spectra of $[Cu(dbp)(dmp)](PF_6)$ [solid line] and $[Ru(bpy)_3](PF_6)_2$ [dashed line] at $\lambda^{ex}$=455 nm. An inset is also illustrated, of the corrected solid state emission spectra of both complexes at $\lambda^{ex}$=450 nm.

It is readily demonstrated that the [Cu(dbp)(dmp)](PF$_6$) complex is brightly photoluminescent at room temperature upon illumination with a hand-held UV lamp. Since many of the applications of photoluminescent inorganic complexes require the complexes attached to solid supports or embedded in solid matrices, the behavior of the complex in the solid state has been studied and compared with [Ru(bpy)$_3$](PF$_6$)$_2$. The excited-state lifetime and emission spectra of the complex and [Ru(bpy)$_3$](PF$_6$)$_2$ were recorded at room temperature upon excitation into the absorption band ($\mathring{A}_{max}^{abs}$= 454 nm, mineral oil mull), with ground samples of each on Whatman #50 filter paper. The present complex is photoluminescent with a maximum at 595 nm, and the decay is best fit by multiple exponentials. The quantum yield of the complex was determined using an established protocol [Wrighton et al., *J. Phys. Chem.*, 78:2229–2233 (1974)] and found to be 1.19±0.25 times higher than [Ru(bpy)$_3$](PF$_6$)$_2$ under ambient conditions. We estimate the solid-state quantum yield of the complex is at least 50 times higher than that of one of the most emissive, previously examined [Cu (NN$_2$)]$^+$complexes, [Cu(bfp)$_2$](PF$_6$) (bfp=2,9-bis (trifluoromethyl)-1,10 -phenanthroline). Further, the solid-state lifetime of the complex is considerably longer than that found for [Ru(bpy)$_3$](PF$_6$)$_2$ (FIG. 2).

Figure 3:
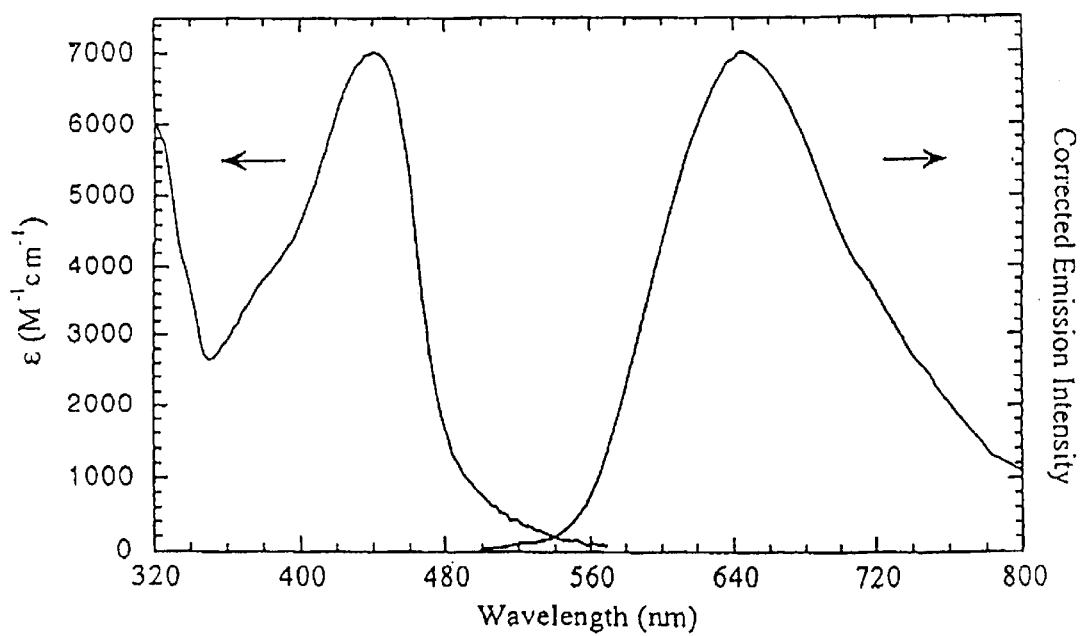
FIG. 3 is a graph illustrating the absorption spectrum and corrected emission spectrum at $\lambda^{ex}$=450 nm for the complex of FIG. 1 in dichloromethane at room temperature.

The absorption and emission spectra of the complex were recorded in CH$_2$Cl$_2$ (FIG. 3) The absorption bands centered at 440 nm ($\epsilon$=7000 M$^{-1}$ cm$^{-1}$) are assigned to MLCT transitions, analogous to those of [Cu(dmp)$_2$]$^+$. The complex is photoluminescent in CH$_2$Cl$_2$ with an emission maximum at 646 nm; the absolute quantum yield is 1.0%. The excited-state lifetime of the complex in degassed CH$_2$Cl$_2$ is 0.73 μs, as determined with excitation at 445 nm or 455 nm with observation at 675 nm or 690 nm, with the error in τ estimated to be ±5%. In the prior art, the longest excited-state lifetime and largest quantum yield for a [Cu(NN)$_2$]$^+$ complex in solution were found for [Cu(dsbp)$_2$]$^+$(dsbp=2, 9-di-sec-butyl-1,10-phenanthroline): τ=0.40 μs and φ=0.45%. (Eggleston et al., supra). Relative to [Cu(dsbp)$_2$]$^+$, the complex exhibits an 82% increase in τ and a 120% increase in φ.

Although the complex is stable in CH$_2$Cl$_2$ and MeOH, upon dissolution in CH$_3$CN or DMSO it readily dissociates to [Cu(dmp)$_2$]$^+$, [Cu(dbp)S$_2$]$^+$(S=solvent) and dbp. Heteroleptic copper(l) bis(diimine) complexes are known to be usually stable to dissociation/scrambling in various solvents, provided that one of the ligands is sterically incapable of forming bis complexes. In the case of [Cu(dbp)(dmp)]$^+$, we believe that dissociation occurs in CH$_3$CN or DMSO because the stability of the heteroleptic complex is not high enough to offset the formation of [Cu(dbp)S$_2$]$^+$.

The complexes of the present invention can, as noted, be utilized for numerous applications which take advantage of the photoluminescent properties and the fact that the degree of quenching of such luminescence provides a quantitative means of detection of various substances. For instance, the complexes can be used to detect and quantify the concentration of oxygen, ammonia, nitric oxide and nitrogen dioxide molecules in liquids and gases (i.e., liquid and gas phases) by contacting one or more such complexes with the liquid or gas to be analyzed. Conveniently the complexes used in such applications can be attached to solid supports for such contacts. Other potential uses involve contact of the complexes with respective materials to produce visible photosensitization of titanium dioxide, to sensitize dyes for photovoltaic devices/solar cells and to produce hydrogen by photochemically splitting water.

As an example, the copper(I) bis(phenanthroline) complex [Cu(dbp)(dmp)[PF$_6$)—(dbp=2,9-di-tert-butyl-1,10-phenanthroline; dmp=2,9-dimethyl-1,10-phenanthroline) was immobilized in polystyrene, and the polystyrene films were examined as luminescent solid-state oxygen sensors. The emission spectra of the films were examined under varying concentrations of oxygen. Significant quenching of the luminescent signal was observed under pure oxygen, and it was determined that oxygen could be measured over the 0–760 Torr range. The films showed a high degree of reproducibility over numerous runs, and a Stern-Volmer plot showed that the quenching response was linearly dependent on oxygen concentration. This represents the first use of an immobilized copper complex for the optical detection of oxygen. This is an important improvement over previous ruthenium-based luminescent sensors since copper-based sensors can be prepared at a fraction of the cost of the latter, while providing equal or superior detection capability.

Therefore, the development of the complexes of this invention and their methods of formation and use represent a significant improvement in the photophysics of [Metal (NN)$_2$]$^+$ complexes. This invention demonstrates that inexpensive metal-based heteroleptic complexes can exhibit photophysical properties that are equivalent to, or better than, the prior art costly ruthenium-based homoleptic complexes.

It will be evident that there are numerous embodiments which are not expressly set forth above but which are clearly within the scope and spirit of the invention. The above description should therefore be considered to be exemplary only, and the scope of the invention is to be limited solely by the appended claims.

We claim:

1. A complex being heteroleptic and comprising a metal bound to a first ligand and a second ligands, each ligand having a pair of substituents with said substituents on said first ligand being different from the substituents on said second ligand, one of said ligands being of a size and shape which prevents two of that ligand from forming a homoleptic complex with said metal, and said different ligands not interfering sterically with each other.

2. A complex as in claim 1 wherein said metal comprises copper, silver, zinc or lithium or an analog thereof.

3. A complex as in claim 1 wherein each said ligand comprises a hydrocarbon or substituted hydrocarbon compound.

4. A complex as in claim 3 wherein substituents on said substituted hydrocarbon compound are disposed terminally of said substituted hydrocarbon compound.

5. A complex as in claim 3 wherein said substituted hydrocarbon comprises a hydrocarbon compound containing at least one alkyl, aryl, or alkaryl or halogen-, chalcogen-, nitrogen- or phosphorus-containing moiety or a heteroatom.

6. A complex as in claim 3 wherein at least one of said ligands comprises phenanthroline or a substituted phenanthroline compound.

7. A complex as in claim 1 having the property of photoluminescence.

* * * * *